(12) United States Patent
Fan et al.

(10) Patent No.: US 8,093,260 B2
(45) Date of Patent: Jan. 10, 2012

(54) APORPHINE DERIVATIVES AND PHARMACEUTICAL USE THEREOF

(75) Inventors: Chin-Tsai Fan, Sinying (TW);
Cheng-Shun Lai, Sinying (TW);
Mei-Jung Lin, Sinying (TW)

(73) Assignee: Standard Chem. & Pharm. Co., Ltd., Sinying (TW)

( * ) Notice: Subject to any disclaimer, the term of this patent is extended or adjusted under 35 U.S.C. 154(b) by 427 days.

(21) Appl. No.: 12/457,714

(22) Filed: Jun. 19, 2009

(65) Prior Publication Data

US 2009/0318489 A1 Dec. 24, 2009

Related U.S. Application Data

(60) Provisional application No. 61/074,246, filed on Jun. 20, 2008.

(51) Int. Cl.
*A61K 31/473* (2006.01)
*C07D 221/18* (2006.01)

(52) U.S. Cl. .......................................... 514/284; 546/75

(58) Field of Classification Search .................. 514/284; 546/75

See application file for complete search history.

(56) References Cited

U.S. PATENT DOCUMENTS

| 4,120,964 | A | 10/1978 | Hartenstein et al. |
| 4,202,980 | A | 5/1980 | Hartenstein et al. |
| 6,313,134 | B1 | 11/2001 | Su et al. |
| 7,057,044 | B2 | 6/2006 | Su et al. |
| 7,294,715 | B2 | 11/2007 | Su et al. |

FOREIGN PATENT DOCUMENTS

FR 2130107 A5 * 11/1972

OTHER PUBLICATIONS

Cai, Hua et al., Endothelial Dysfunction in Cardiovascular Diseases: the Role of Oxidant Stress, Circulation Research, 2000, p. 840-844, 87, American Heart Association, United States.
Roberts, Christian K. et al., Oxidative Stress and Metabolic Syndrome, Life Sciences, 2009, p. 705-712, 84, Elsevier Inc.
Solov'Eva Eiu et al., Zh Nevrol Psikhiatr Im S S Korsakova, 2008, p. 37-42, 108(6).
Warnholtz, Ascan et al., Increased NADH-Oxidase-Mediated Superoxide Production in the Early Stages of Atherosclerosis: Evidence for Involvement of the Renin-Angiotensin System, 1999, p. 2027-2033, 99, American Heart Association, United States.
Berlinder, Judith A. et al., The Role of Oxidized Lipoproteins in Atherogenesis, Free Radical Biology & Medicine, 1996, p. 707-727, vol. 20, No. 5, Elsevier Science Inc., United States.
Heinecke, Jay W., Oxidants and Antioxidants in the Pathogenesis of Atherosclerosis: Implications for the Oxidized Low Density Lipoprotein Hypothesis, Atherosclerosis, 1998, p. 1-15, 141, Elsevier Science Ireland Ltd.
Patterson, Cam et al., The Oxidative Paradox: Another Piece in the Puzzle, Circulation Research, 2000, p. 1074-1076, 87, American Heart Association, United States.
Li, Dayuan et al., Expression of Lectin-Like Oxidized Low-Density Lipoprotein Receptors during Ischemia-Reperfusion and its Role in Determination of Apoptosis and Left Ventricular Dysfunction, Journal of the American College of Cardiology, 2003, p. 1048-1055, vol. 41, No. 6, Elsevier Inc.
Teng, Che-Ming et al., Vasoconstricting Effect in Rat Aorta caused by Thaliporphine Isolated from the Plant *Nelistsea konishii* K, European Journal of Pharmacology, 1993, p. 7-12, 233, Elsevier Science Publishers.
Su, Ming-Jai et al., Thaliporphine, a Positive Inotropic Agent with a Negative Chronotropic Action, European Journal of Pharmacology, 1994, p. 141-150, 254, Elsevier Science.
Hung, Li-Man et al., Thaliporphine Protects Ischemic and Ischemic-Reperfused Rat Hearts via an NO-Depedent Mechanism, Drug Development Research, 2001, p. 446-453, 52, Wiley-Liss, Inc.
Chiao, Chin-Wei et al., Thaliporphine Increases Survival Rate and Attenuates Multiple Organ Injury in LPS-Induced Endotoxaemia, Naunyn-Schmiedeberg's Arch Pharmacol, 2005, p. 34-43, 371, Springer-Verlag.
Mansuy, Daniel et al., A New Potent Inhibitor of Lipid Peroxidation in Vitro and in Vivo, the Hepatoprotective Drug Anisyldithiolthione, Biochemical and Biophysical Research Communications, 1986, p. 1015-1021, vol. 135, No. 3, Academic Press, Inc.
Tsuchiya, Masahiko et al., Antioxidant Radical-Scavenging Activity of Carotenoids and Retinoids Compared to α-Tocopherol, Methods in Enzymology, 1992, p. 460-472, 213, Academic Press, Inc.

* cited by examiner

*Primary Examiner* — Charanjit Aulakh
(74) *Attorney, Agent, or Firm* — Hsiu-Ming Saunders; Intellectual Property Connections, Inc.

(57) ABSTRACT

The present invention discloses novel aporphine derivatives. Also, the present invention discloses that these novel aporphine derivatives can be used for treating oxidative stress induced diseases such as cardiovascular disease, diabetes, aging, Alzheimer's disease, kidney disease, cancer or brain ischemic disease etc.

20 Claims, 3 Drawing Sheets

APORPHINE DERIVATIVES AND PHARMACEUTICAL USE THEREOF

CROSS-REFERENCE TO RELATED APPLICATION

This application claims the benefit of the filing date of U.S. Provisional Application Ser. No. 61/074,246, entitled "APORPHINE DERIVATIVES, APORPHINE DERIVATIVES SALTS AND THEIR PHARMACEUTICAL USES" filed Jun. 20, 2008 under 35 USC & 119(e)(1).

BACKGROUND OF THE INVENTION

1. Field of the Invention

The present invention relates to aporphine compounds and pharmaceutical use thereof, more particularly, to aporphine compounds that can inhibit lipid peroxidase, exert the free radical scavenging activities and protect vascular smooth muscle cells, and pharmaceutical use thereof.

2. Description of Related Art

Oxidative stress alters many functions of the endothelium. As known in the art, oxidative stress is involved in the pathogenesis of a group of diseases, such as hypercholesterolemia, atherosclerosis, hypertension, diabetes, and heart failure etc. (Cai H et al., Circ. Res. 2000; 87: 840-844), and ischemic cerebral diseases, including ischemic cerebral thrombosis, ischemic cerebral embolism, hypoxic ischemic encephalopathy etc. Department of Physiological Science. University of California also published that oxidative stress is thought to play a major role in the pathogenesis of a variety of human diseases, including atherosclerosis, diabetes, hypertension, aging, Alzheimer's disease, kidney disease and cancer (Roberts C K et al., Life Sci. 2009; 84: 705-712). In addition, a role of the free-radical processes and disturbances of oxidative-restorative blood homeostasis and nervous tissue in the pathogenesis of brain ischemic pathology and other diseases was published (Solov'eva Elu et al., Zh Nevrol Psikhiatr Im S S Korsakova. 2008; 108(6): 37-42). Recent studies also demonstrated a significant role of inflammatory processes and oxidative stress in the pathomechanism of cerebral stroke. Increased production of free radicals was observed in both the ischemic and haemorrhagic strokes and oxidative stress was shown to be one of the causative mechanisms of tissue damage in these diseases.

Oxidative stress mediates cell damage via reactive oxygen species (ROS). Oxidative stress has been identified throughout the process of atherogenesis (Warnholtz A et al., Circulation 1999; 99: 2027-2033). As the process of atherogenesis proceeds, inflammatory cells as well as other constituents of the atherosclerotic plaque release large amounts of ROS, which further facilitate atherogenesis. In general, increased production of ROS may affect four fundamental mechanisms that contribute to atherogenesis: oxidation of low density lipoprotein (LDL), endothelial cell dysfunction, growth of the vascular smooth muscle cells and monocytes migration (Berliner J A et al., Free Radic Biol Med 1996; 20: 707-727). Therefore, oxidative stress plays a decisive role in atherosclerosis. A number of studies suggest that ROS oxidatively modified LDL is a more potent proatherosclerotic mediator than the native unmodified LDL (Heinecke J W., Atherosclerosis 1998; 141: 1-15).

Atherosclerosis is the buildup of fatty deposits called plaque on the inside walls of arteries. Arteries are blood vessels that carry oxygen and blood to the heart, brain, and other parts of the body. As plaque builds up in an artery, the artery gradually narrows and can become clogged. As an artery becomes more and more narrowed, less blood can flow through.

Risk factors for atherosclerosis, such as hypertension and hyperlipidemia, are also associated with increased generation of ROS (Patterson C et al., Circ. Res. 2000; 87(12): 1074-1076). Increasing evidence shows that ischemia-reperfusion, which frequently occurs in narrowed atherosclerotic arteries, increases ROS generation (Li D et al., J Am Coll Cardiol 2003; 41: 1048-1055).

Thaliporphine, which is a phenolic alkaloid isolated from the plants of Neolitsea konishii K, is an aporphine derivative. (Teng C M et al., Eur J Pharmacol. 1993; 233(1): 7-12). It has been disclosed that thaliporphine is a positive inotropic agent with a negative chionotropic action (Su M J et al., Eur. J. Pharmacol, 1994; 254: 141-150). In animal coronary artery occlusion study, thaliporphine reduces occurrence of arrhythmia and mortality during ischemia and ischemia-reperfusion. It also attenuates cardiac infarct zone after long term ischemia. Besides, thaliporphine inhibits low density lipoprotein (LDL) peroxidation and exerted the scavenging activities of superoxide anion. Particularly, thaliporphine significantly increases NO and decreases lactate dehydrogenase (LDH) levels in the blood during the end period of ischemia or ischemia-reperfusion (I/R). Thus, thaliporphine can reduce ischemia or I/R-induced cardiac injury. Accordingly, the multifactorial beneficial effects of thaliporphine may afford an opportunity of being used as an effective antiarrhythmic and cardioprotective agent (Hung L M et al., Drug Dev. Res. 2001; 52: 446-453). In addition, thaliporphine could be a novel agent for attenuating endotoxin-induced circulatory failure and multiple organ injury, and may increase the survival rate (Chiao C W et al., Naunyn Schmiedebergs Arch Pharmacol. 2005; 371(1): 34-43).

U.S. Pat. No. 6,313,134 disclosed thaliporphine and its derivatives for the treatment and/or prophylaxis of cardiac diseases, including cardiac arrhythmia, myocardial ischemia or myocardial infarction, and sudden death caused by cardiac arrhythmia or acute myocardial infarction.

U.S. Pat. No. 7,057,044 provided aporphine and oxoaporphine compounds that have endothelial nitric oxide synthase (eNOS) maintaining or enhancing activities and may be used to manufacture a medicaments for preventing or treating ischemic diseases in human and mammal, and the ischemic diseases may include ischemic cerebral apoplexy, ischemic cerebral thrombosis, ischemic cerebral embolism, hypoxic ischemic encephalopathy, ischemic cardiac disease or ischemic enteropathy etc.

SUMMARY OF THE INVENTION

The object of the present invention is to provide novel aporphine derivatives that are effective in inhibiting lipid peroxidase, exerting the free radical scavenging activities and protecting blood vessel smooth muscle cells and thus can reduce oxidative stress which may induce diseases, such as hypercholesterolemia, atherosclerosis, hypertension and heart failure, diabetes, aging, Alzheimer's disease, kidney disease, cancer or brain ischemic diseases etc.

To achieve the object, the present invention provides a novel compound of the following formula (I):

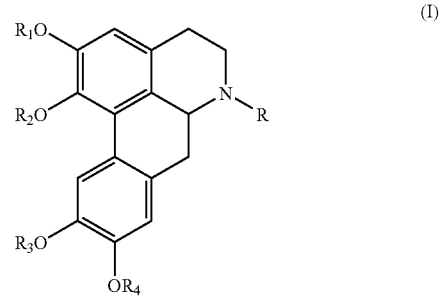

wherein
each of $R_1$, $R_2$, $R_3$ and $R_4$, independently, is hydrogen, $C_{1-6}$ alkyl, or —C(O)R$_5$;

R is hydrogen, $C_{1-6}$ alkyl, —C(O)R$_5$, or $C_{1-6}$ alkyl substituted by the following group: —C(O)OR$_6$, —C(O)NR$_6$R$_7$, at least one of —OR$_6$, at least one of —NR$_6$R$_7$, $C_{4-9}$ heteroaryl containing at least one heteroatom selected from the group consisting of N, O and S, $C_{4-9}$ heterocyclyl containing at least one heteroatom selected from the group consisting of N, O and S, or $C_{6-10}$ aryl unsubstituted or substituted by at least one selected from the group consisting of halogen, hydroxyl, $C_{1-6}$ alkoxy and $C_{1-6}$ alkyl;

$R_5$ is $C_{4-9}$ heteroaryl containing at least one heteroatom selected from the group consisting of N, O and S, or $C_{1-16}$ alkyl substituted by —N$_6$R$_7$ or $C_{4-9}$ heterocyclyl containing at least one heteroatom selected from the group consisting of N, O and S;

each of $R_6$ and $R_7$, independently, is hydrogen, $C_{1-6}$ alkyl, $C_{4-9}$ heteroaryl containing at least one heteroatom selected from the group consisting of N, O and S, $C_{4-9}$ heterocyclyl containing at least one heteroatom selected from the group consisting of N, O and S, or $C_{6-10}$ aryl unsubstituted or substituted by at least one selected from the group consisting of halogen, hydroxyl, $C_{1-6}$ alkoxy and $C_{1-6}$ alkyl;

with the proviso that at least one of $R_1$, $R_2$, $R_3$ and $R_4$ is —C(O)R$_5$, when R is hydrogen, $C_{1-16}$ alkyl, $C_{1-2}$ alkyl substituted by —OR$_8$, or $C_{1-6}$alkyl substituted by $C_{6-10}$ aryl unsubstituted or substituted by at least one selected from the group consisting of halogen, hydroxyl, $C_{1-6}$ alkoxy and $C_{1-6}$ alkyl, wherein $R_8$ is phenyl unsubstituted or substituted by at least one selected from the group consisting of halogen, hydroxyl, $C_{1-6}$ alkoxy and $C_{1-6}$ alkyl.

Referring to Formula (I), preferably, each of $R_1$, $R_2$, $R_3$ and $R_4$, independently, is hydrogen or $C_{1-6}$ alkyl, and R is —C(O)R$_5$, or $C_{1-6}$ alkyl substituted by —C(O)OR$_6$, —C(O)NR$_6$R$_7$, two of —OR$_6$ or $C_{4-9}$ heteroaryl containing at least one heteroatom selected from the group consisting of N, O and S.

Referring to Formula (I), more preferably, each of $R_1$, $R_2$, $R_3$ and $R_4$, independently, is hydrogen or $C_{1-6}$ alkyl, and R is —C(O)R$_5$, or $C_{1-6}$ alkyl substituted by C(O)OR$_6$, —C(O)NR$_6$R$_7$, $C_{4-9}$ heteroaryl containing at least one heteroatom selected from the group consisting of N, O and S, or both of hydroxyl and —O—C$_{6-10}$ aryl unsubstituted or substituted by at least one selected from the group consisting of halogen, hydroxyl, $C_{1-6}$ alkoxy and $C_{1-6}$ alkyl.

Referring to Formula (I), most preferably, each of $R_1$, $R_2$, $R_3$ and $R_4$, independently, is hydrogen or $C_{1-6}$ alkyl, and R is —C(O)R$_5$, or $C_{1-6}$ alkyl substituted by —C(O)NR$_6$R$_7$, $C_{4-9}$ heteroaryl containing at least one heteroatom selected from the group consisting of N, O and S, or both of hydroxyl and —O—C$_{6-10}$ aryl unsubstituted or substituted by at least one selected from the group consisting of halogen, hydroxyl, $C_{1-6}$ alkoxy and $C_{1-6}$ alkyl. Herein, preferably, $R_6$ is hydrogen, and $R_7$ is $C_{4-9}$ heteroaryl containing at least one heteroatom selected from the group consisting of N, O and S, $C_{4-9}$ heterocyclyl containing at least one heteroatom selected from the group consisting of N, O and S, or $C_{6-10}$ aryl unsubstituted or substituted by at least one selected from the group consisting of halogen, hydroxyl, $C_{1-6}$ alkoxy and $C_{1-6}$ alkyl.

Referring to Formula (I), specifically, R can be

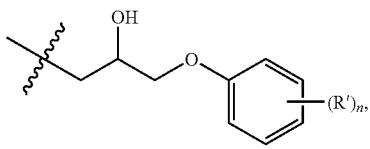

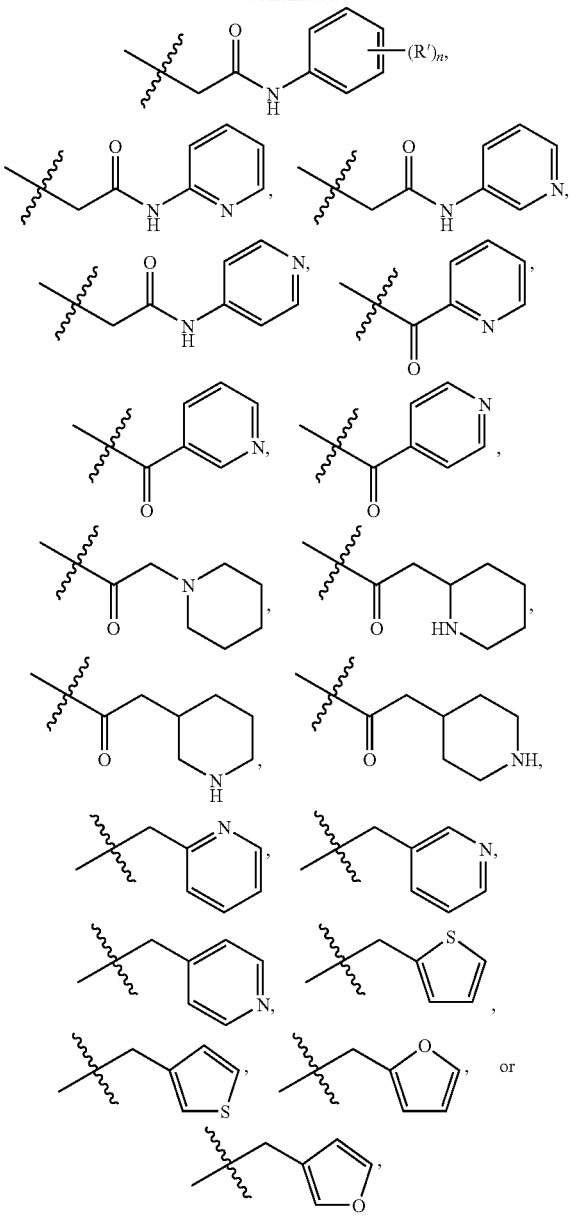

n being an integer from 0 to 5, and R' independently being halogen, hydroxyl, $C_{1-6}$ alkoxy or $C_{1-6}$ alkyl.

The above-mentioned compounds are novel and effective in inhibiting lipid peroxidase, exerting the free radical scavenging activities and protecting vascular smooth muscle cells and thus can substantially improve oxidative stress and protect endothelium cells.

Thus, another aspect of this invention relates to a pharmaceutical composition for treating oxidative stress induced diseases, comprising an effective amount of the above-mentioned compounds. Herein, the oxidative stress induced diseases include, for example, hypercholesterolemia, atherosclerosis, hypertension and heart failure, diabetes, aging, Alzheimer's disease, kidney disease, cancer or brain ischemic disease, etc.

In the present invention, the term "alkyl" refers to a straight or branched hydrocarbon. Examples of alkyl include, but are not limited to, methyl, ethyl, n-propyl, i-propyl, n-butyl, i-butyl, and t-butyl.

In the present invention, the term "aryl" refers to a 6-carbon monocyclic, 10-carbon bicyclic aromatic ring system wherein each ring may have 1 to 4 substituents. Examples of aryl groups include, but are not limited to, phenyl and naphthyl.

In the present invention, the term "alkoxy" refers to an —O-alkyl radical. Examples of alkoxy include, but are not limited to, methoxy, ethoxy, n-propoxy, isopropoxy, n-butoxy, iso-butoxy, sec-butoxy, and tert-butoxy.

In the present invention, the term "heterocyclyl" refers to a nonaromatic ring system having at least one heteroatoms (such as O, N, or S). Examples of heterocyclyl groups include, but are not limited to, piperidinyl, piperazinyl, pyrrolidinyl, dioxanyl, morpholinyl, and tetrahydrofuranyl.

In the present invention, the term "heteroaryl" refers to a hydrocarbon ring system (mono-cyclic or bi-cyclic) having at least one aromatic ring which contains at least one heteroatom such as O, N, or S as part of the ring system and the reminder being carbon. Examples of heteroaryl moieties include, but are not limited to, furyl, pyrrolyl, thienyl, oxazolyl, imidazolyl, thiazolyl, pyridinyl, pyrimidinyl, benzimidazolyl, benzothiazolyl, coumarinyl, quinazolinyl, and indolyl.

Exemplary compounds of the formula (I) are shown below.

Also within the scope of this invention is a method for treating oxidative stress induced diseases (such as cardiovascular diseases, diabetes, aging, Alzheimer's disease, kidney disease, cancer or brain ischemic diseases etc.) by administering to a subject in need thereof an effective amount of a compound of the formula (I), as well as the use of such a composition for manufacture of a medicament for treating oxidative stress induced diseases (such as hypercholesterolemia, atherosclerosis, hypertension and heart failure, diabetes, aging, Alzheimer's disease, kidney disease, cancer or brain ischemic diseases etc.).

To practice the method of the present invention, a composition having one or more of the above-described compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A composition for oral administration can be any orally acceptable dosage form including granules, pellets, capsules, tablets, emulsions and aqueous suspensions, dispersions, and solutions.

In the present invention, the pharmaceutical composition can further comprise a pharmaceutical acceptable carrier.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound of the formula (I).

Other objects, advantages, and novel features of the invention will become more apparent from the following detailed description when taken in conjunction with the accompanying drawings.

DETAILED DESCRIPTION OF THE PREFERRED EMBODIMENT

Figure 1:
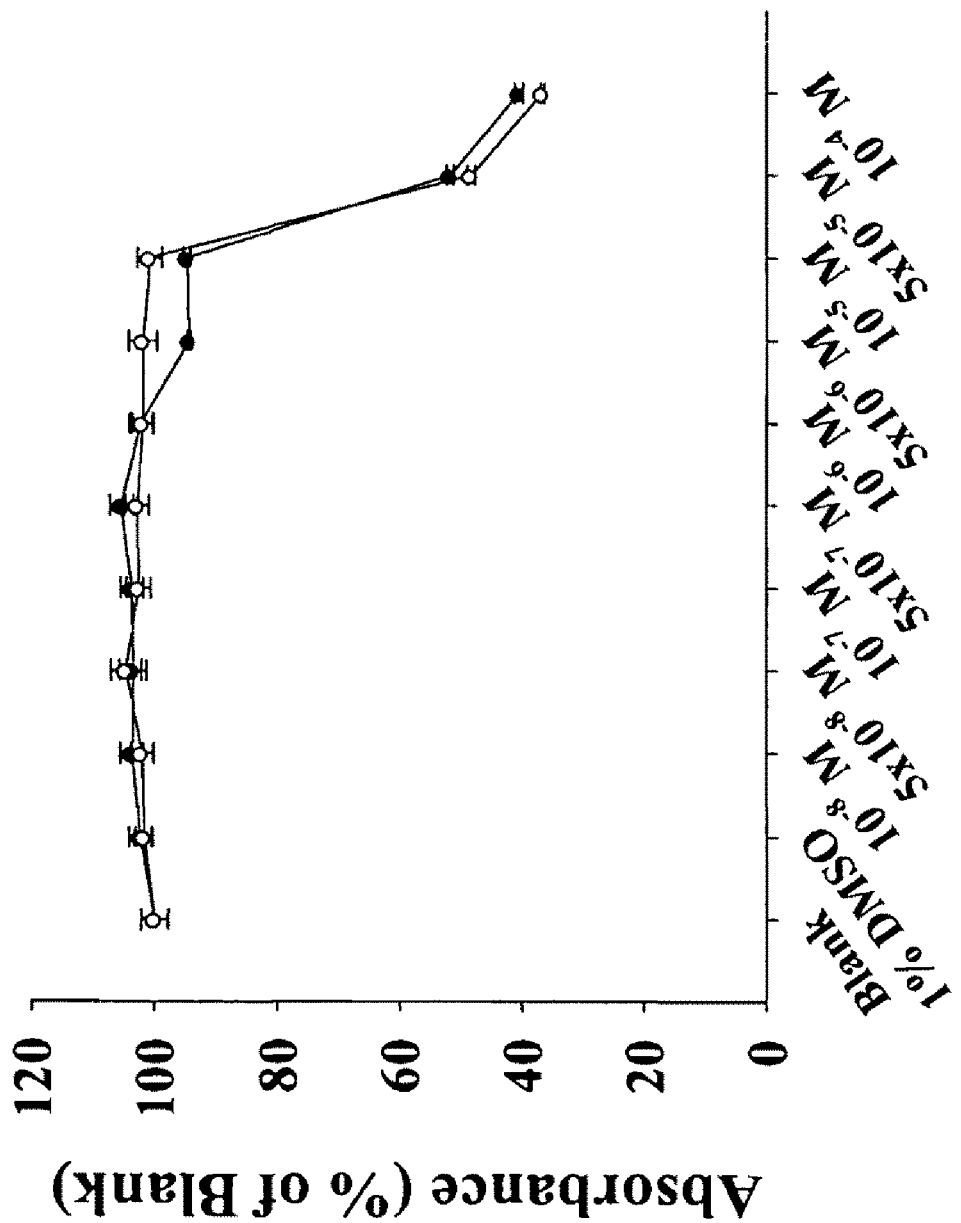
FIG. 1 shows a diagram of absorbance of DPPH versus the concentration of Compounds 1 and 2 (-■—for Compound 1, -○—for Compound 2).

Northaliporphine can be found within the U.S. Pat. No. 4,202,980, norglaucine can be found within the U.S. Pat. No. 4,120,964, boldine, thaliporphine, glaucine, laurolitsine, can be employed as the starting material to generate the aporphine derivatives of the general formula (I). The boldine is available from the market, the thaliporphine and the glaucine can be synthesized according to U.S. Pat. No. 6,313,134 B1, and the norglaucine, the northaliporphine and the laurolitsine can be synthesized according to U.S. Pat. No. 7,294,715 B2.

An acylation or alkylation reaction may be involved in the preparation of the aporphine derivatives. These various aporphine derivatives can be achieved by various approaches (eg. Acylation by acyl halide, acyl anhydride, or mixed anhydride; alkylation from a suitable alkylating agent, reductive amination from a suitable aldehyde and hydrogenation from a suitable imine, etc.). By using the above preparation processes, the general formula (I) can be synthesized.

In addition, theses above-mentioned exemplary compounds 1-7 can be obtained by the following synthesis schemes 1-7, respectively.

EXAMPLE 1

Preparation of Compound 1

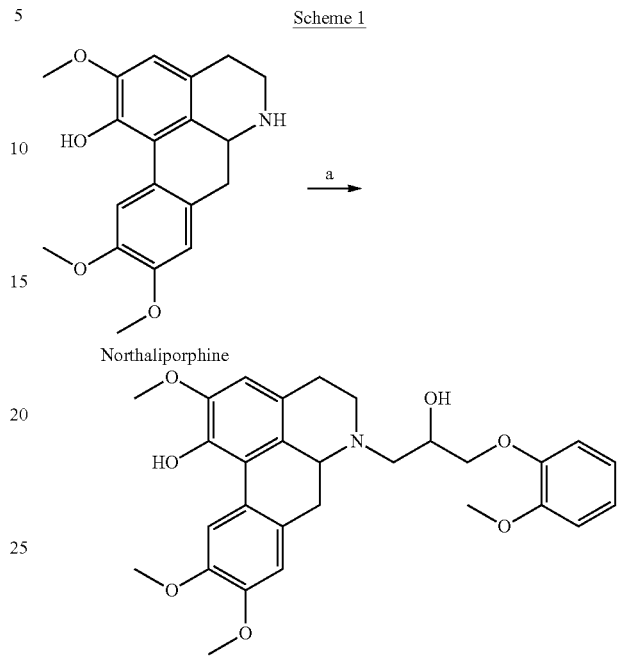

Reagents and conditions:
(a) 2-[(2-methoxy-phenox)methyl] oxirane, MeOH, 70° C., 16 hrs.

Northaliporphine (380 mg, 1.16 mmol), methanol (MeOH, 10 mL) and 2-[(2-methoxy-phenox)methyl]oxirane (167 mg, 0.92 mmol) were added into a 50 mL round bottom flask and stirred at 70° C. for 16 hours. The mixture was evaporated to dryness. The residue was purified by chromatography (silica gel: 70-230 mesh 30 g, mobile phase: 2% MeOH/$CH_2Cl_2$, v/v) to obtain Compound 1, $R_f$ 0.15 (2% MeOH/$CH_2Cl_2$, v/v); Physical data were as follows: mp: 63-68° C. ($CH_2Cl_2$); IR(KBr) $v_{max}$: 3500, 2931, 1605, 1506, 1464, 1253, 1112 cm⁻¹; ¹H NMR ($CDCl_3$, 500 MHz): δ 8.00 (s, 1H), 6.98-6.88 (m, 4H), 6.75 and 6.73 (s, 1H), 6.53 (s, 1H), 6.12 (brs, 1H), 4.24-4.07 (m, 3H), 3.90 (s, 3H), 3.88 (s, 3H), 3.85 (s, 3H), 3.79 (s, 3H), 3.39-2.53 (m, 9H); EIMS (70 eV): m/z (%) 507 [M]⁺, 339 (100).

EXAMPLE 2

Preparation of Compound 2

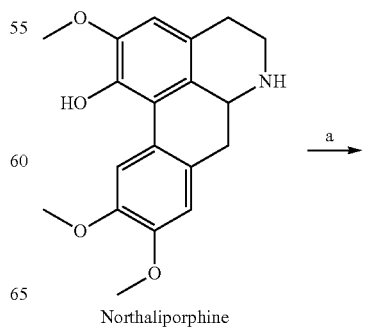

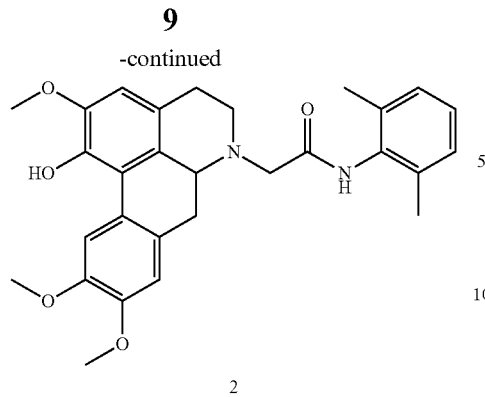

2

Reagents and conditions:
(a) 2-chloro-N-(2,6-dimethyl-phenyl) acetamide, Et₃N, MeOH, 60° C., 2 days.

Northaliporphine (260 mg, 0.794 mmol), MeOH (10 mL) and 2-chloro-N-(2,6-dimethyl-phenyl)acetamide (187 mg, 0.946 mmol) were added into a 50 mL two-necked round bottom flask. Then triethylamine (Et₃N, 0.5 mL, 3.55 mmol) was dropped into the mixture, and the reaction was allowed to proceed at 60° C. for two days. The mixture was evaporated to dryness. The residue was partitioned with water (50 mL) and dichloromethane (50 mL×3), and the organic layers were collected. The organic layer was dried with anhydrous MgSO₄ and then filtered. The filtrate was evaporated to dryness. The residue was purified by chromatography (silica gel: 70-230 mesh 30 g, mobile phase: 2% MeOH/CH₂C₂, v/v) to obtain Compound 2, $R_f$ 0.58 (2% MeOH/CH₂Cl₂, v/v); Physical data were as follows: mp: 205-207° C. (CH₂Cl₂); IR(KBr) $v_{max}$: 3312, 2945, 1663, 1604, 1511, 1477, 1258, 1087 cm$^{-1}$; $^1$H NMR (CDCl₃, 500 MHz): δ 8.99 (s, 1H), 8.02 (s, 1H), 7.10 (s, 3H), 6.76 (s, 1H), 6.56 (s, 1H), 6.12 (s, 1H), 3.91 (s, 9H), 3.77-3.11 (m, 5H), 2.98-2.86 (m, 2H), 2.75-2.69 (m, 2H), 2.25 (s, 6H); EIMS (70 eV): m/z (%) 488 [M]$^+$, 326 (100).

EXAMPLE 3

Preparation of Compound 3

Scheme 3

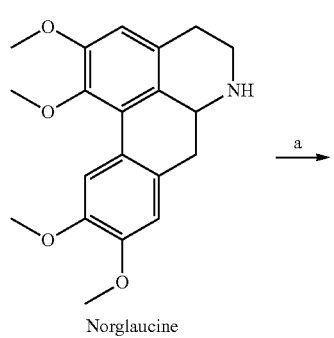

Norglaucine

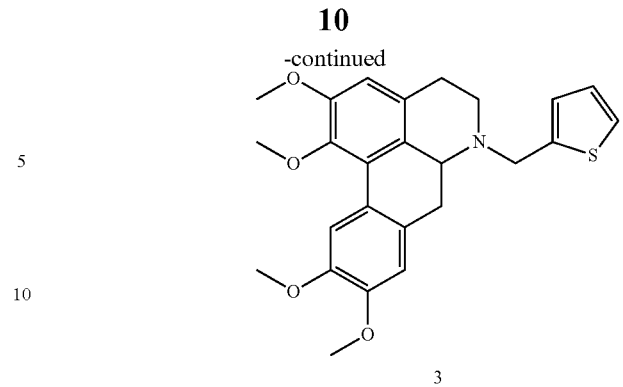

3

Reagents and conditions:
(a) 2-thiophenecarboxaldehyde, MgSO₄, MeOH, AcOH, NaBH₃CN, 70° C., 4 hrs.

Norglaucine (300 mg, 0.88 mmol), MgSO₄ (1 g), MeOH (7 mL), 2-thiophenecarboxaldehyde (0.14 mL, 1.5 mmol) and AcOH (0.5 mL, 8.88 mmol) were added into a 100 mL two-necked round bottom flask and stirred at room temperature. Sodium cyanoborohydride (NaBH₃CN, 100 mg, 1.58 mmol) was added into the mixture after 1 hour, and the reaction was allowed to proceed at 70° C. for 4 hours. The mixture was evaporated to dryness. The residue was partitioned with water (50 mL) and dichloromethane (50 mL×2), and the organic layers were collected. The organic layer was dried with anhydrous MgSO₄ and then filtered. The filtrate was evaporated to dryness. The residue was purified by chromatography (silica gel: 230-400 mesh 30 g, mobile phase: EA/Hex=1/2, v/v) to obtain Compound 3, $R_f$ 0.77 (EA/Hex=1/1, v/v); Physical data were as follows: mp: 143-148° C. (CH₂Cl₂); IR(KBr) $v_{max}$: 2958, 1578, 1514, 1466, 1110 cm$^{-1}$; $^1$H NMR (CDCl₃, 400 MHz): δ8.05 (s, 1H), 7.22-7.20 (m, 1H), 6.96-6.95 (m, 2H), 6.77 (s, 1H), 6.57 (s, 1H), 4.35 (d, J=14.6 Hz, 1H), 3.92 (s, 3H), 3.88 (s, 3H), 3.86 (s, 3H), 3.85 (d, J=14.6 Hz, 1H), 3.62 (s, 3H), 3.36-3.33 (m, 1H), 3.15-3.09 (m, 2H), 3.05-3.02 (m, 1H), 2.71-2.60 (m, 2H), 2.51-2.44 (m, 1H); EIMS (70 eV): m/z (%) 437 [M]$^+$, 97 (100).

EXAMPLE 4

Preparation of Compound 4

Scheme 4

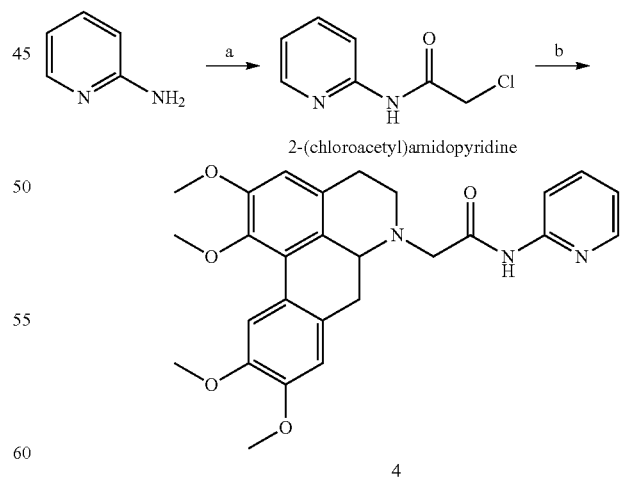

4

Reagents and conditions:
(a) chloroacetyl chloride, Et₃N, CH₂Cl₂, rt, 17 hrs;
(b) Norglaucine, K₂CO₃, CH₃CN, 80° C., 16 hrs.

2-Aminopyridine (2 g, 21.3 mmol), chloroacetyl chloride (2.5 mL, 31.4 mmol) and Et₃N (4.4 mL, 31.8 mmol) were dissolved in dichloromethane (CH$_2$Cl$_2$, 100 mL). The reaction mixture was stirred at room temperature for 17 hours, after which the organic phase was washed with an aqueous solution of NaHCO$_3$ (10%, w/v). The organic layer was dried with anhydrous MgSO$_4$ and then filtered. The filtrate was evaporated to dryness. The residue was purified using flash chromatography (CH$_2$Cl$_2$), yielding 2.46 g (68%) of 2-(chloroacetyl)amidopyridine.

Norglaucine (0.3 g, 0.88 mmol), 2-(chloroacetyl)amidopyridine (0.15 g, 0.88 mmol) and potassium carbonate (K$_2$CO$_3$, 0.3 g, 1.8 mmol) in acetonitrile (CH$_3$CN, 7 mL) was stirred at 80° C. for 16 hours. The mixture was evaporated to dryness. The residue was partitioned with water (50 mL) and dichloromethane (50 mL×2). The organic layer was dried with anhydrous MgSO$_4$ and then filtered. The filtrate was evaporated to dryness. The residue was purified by chromatography (silica gel: 230-400 mesh 30 g, mobile phase: EA/Hex=1:1, v/v) to obtain Compound 4, R$_f$ 0.75 (100% EA); Physical data were as follows: mp: 43-46° C. (CH$_2$Cl$_2$); IR(KBr) v$_{max}$: 3300, 2933, 1693, 1578, 1513, 1434, 1257, 1091 cm$^{-1}$; $^1$H NMR (CDCl$_3$, 400 MHz): δ 9.87 (s, 1H), 8.29-8.24 (m, 2H), 8.04 (s, 1H), 7.73-7.69 (m, 1H), 7.04-7.01 (m, 1H), 6.70 (s, 1H), 6.61 (s, 1H), 3.89 (s, 3H), 3.87 (s, 6H), 3.63 (s, 3H), 3.61 (d, J=17.2 Hz, 1H), 3.46-3.42 (m, 1H), 3.30-3.23 (m, 2H), 3.13-3.08 (m, 1H), 2.92-2.68 (m, 4H); ESI-MS (30 V): m/z (%) 476 [M+H]$^+$ (100).

EXAMPLE 5

Preparation of Compound 5

Scheme 5

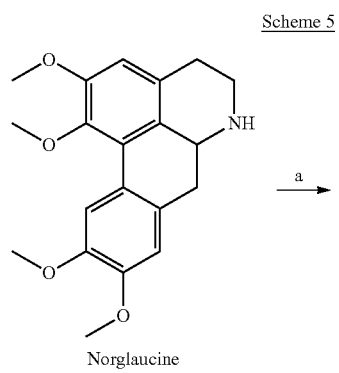

Norglaucine

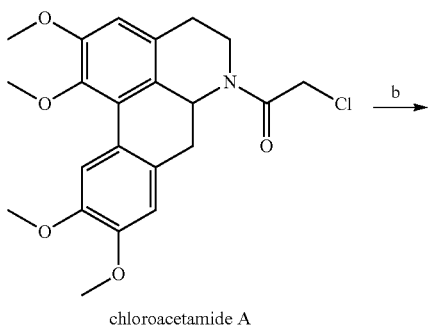

chloroacetamide A

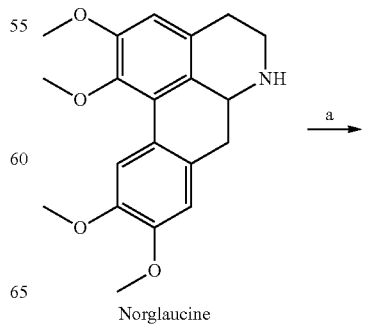

5

Reagents and conditions:
(a) chloroacetyl chloride, Et$_3$N, CH$_2$Cl$_2$, rt, 1 hr;
(b) piperidine, CH$_3$CN, 80° C., 16 hrs.

Norglaucine (500 mg, 1.47 mmol), chloroacetyl chloride (0.35 mL, 4.4 mmol) and CH$_2$Cl$_2$ (7 mL) were added into a 100 mL round bottom flask. Then 0.6 mL of Et$_3$N was dropped into a round bottom flask at room temperature for 1 hour. The reaction solution was poured into 50 mL water, and the mixture was stirred and adjusted with ammonia water to pH 8.0. The mixture was extracted two times with dichloromethane, and the organic layers were collected. The organic layer was dried with anhydrous MgSO$_4$ and then filtered. The filtrate was evaporated to dryness. The residue was purified by chromatography (silica gel: 230-400 mesh 30 g, mobile phase: EA/Hex=1/1, v/v) to obtain chloroacetamide A, R$_f$ 0.46 (EA/Hex=1/1, v/v).

Chloroacetamide A (300 mg, 0.719 mmol) and piperidine (0.5 mL) in CH$_3$CN (7 mL) was stirred at 80° C. for 16 hours and the reaction progress was monitored by silica TLC. The mixture was evaporated to dryness. The residue was partitioned with water (50 mL) and dichloromethane (50 mL×2), and the organic layers were collected. The organic layer was dried with anhydrous MgSO$_4$ and then filtered. The filtrate was evaporated to dryness. The residue was purified by chromatography (silica gel: 230-400 mesh 20 g, mobile phase: EA/Hex=1:1, v/v) to obtain Compound 5, R$_f$ 0.33 (100% EA); Physical data were as follows: mp: 108-110° C. (CH$_2$Cl$_2$); IR(KBr) v$_{max}$: 2934, 1640, 1514, 1451, 1254, 1102 cm$^{-1}$; $^1$H NMR (CDCl$_3$, 400 MHz): δ 8.12 (s, 1H), 6.76 (s, 1H), 6.62 (s, 1H), 5.00-4.00 (m, 2H), 3.89 (s, 3H), 3.88 (s, 6H), 3.65 (s, 3H), 3.33-2.66 (m, 7H), 2.43 (m, 4H), 1.57-1.56 (m, 4H), 1.42 (m, 2H); EIMS (70 eV): m/z (%) 466 [M]$^+$, 381 (100).

EXAMPLE 6

Preparation of Compound 6

Scheme 6

Norglaucine

-continued

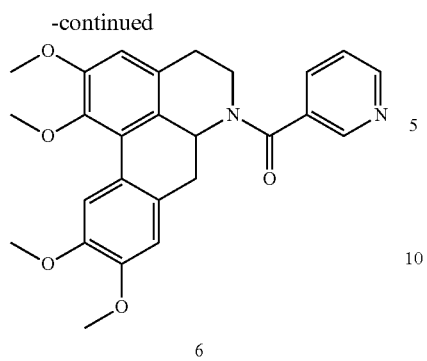

6

Reagents and conditions:
(a) nicotinoyl chloride, Et₃N, CH₃CN, rt, 1 hr.

Nicotinic acid (0.1 g, 0.86 mmol) was heated under reflux with thionyl chloride (1.0 mL, 12.4 mmol) for 1 hour. The solvent was evaporated under reduced pressure. An off-white solid was formed and the product was used immediately for the next step.

Norglaucine (0.2 g, 0.58 mmol) and Et₃N (0.23 mL, 1.56 mmol) were dissolved in CH₃CN (1 mL). The mixture was reacted with nicotinoyl chloride in CH₃CN (1 mL) by adding it drop by drop at room temperature. The mixture was stirred at room temperature for 1 hour, and the solvent was evaporated under reduced pressure. The residue was partitioned with water (10 mL) and dichloromethane (10 mL), and the organic layer was evaporated under reduced pressure. The residue was purified by chromatography (silica gel: 230-400 mesh 15 g, mobile phase: EA/Hex=1:1, v/v) to obtain Compound 6, $R_f$ 0.3 (100% EA); Physical data were as follows: mp: 178-181° C. (CH$_2$Cl$_2$); IR(KBr) $v_{max}$: 2947, 1632, 1514, 1466, 1265, 1099 cm$^{-1}$; $^1$H NMR(CDCl$_3$, 400 MHz): δ 8.70 (s, 1H), 8.67 (brd, J=4.1 Hz, 1H), 8.14 (s, 1H), 7.78 (brd, J=7.7 Hz, 1H), 7.39-7.36 (m, 1H), 6.78 (s, 1H), 6.62 (s, 1H), 3.90 (s, 6H), 3.88 (s, 3H), 3.66 (s, 3H), 3.72-2.64 (m, 6H); EIMS (70 eV): m/z (%) 446 [M]$^+$ (100).

EXAMPLE 7

Preparation of Compound 7

Scheme 7

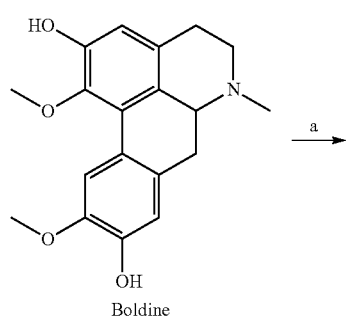

Boldine

-continued

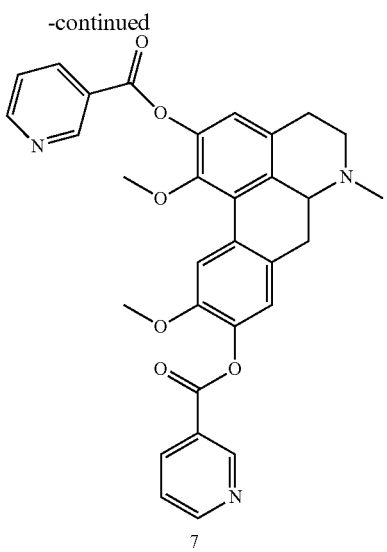

7

Reagents and conditions:
(a) nicotinoyl chloride, Et₃N, toluene, 80° C., 17 hrs.

Nicotinic acid (865 mg, 7 mmol) was heated under reflux with thionyl chloride (3.5 mL, 48.5 mmol) for 1 hour. The solvent was evaporated under reduced pressure. An off-white solid was formed and the product was used immediately for the next step.

Boldine (1 g, 3.1 mmol), nicotinoyl chloride (1 g, 7.1 mmol), Et₃N (1.3 mL, 9.3 mmol) and toluene (12 mL) were added into a 100 mL round bottom flask. The mixture was stirred at 80° C. for 17 hours and the reaction progress was monitored by silica TLC. After removing the salt by filtration, the filtrate was evaporated to dryness. The residue was partitioned with water (75 mL) and dichloromethane (75 mL×3), and the organic layers were collected. The organic layer was dried with anhydrous MgSO$_4$ and then filtered. The filtrate was evaporated to dryness. The residue was purified by chromatography (silica gel: 230-400 mesh 50 g, mobile phase: MeOH/CH$_2$Cl$_2$=1/8, v/v) to obtain Compound 7, $R_f$ 0.58 (MeOH/CH$_2$Cl$_2$=1/6, v/v); Physical data were as follows: mp: 110-113° C. (MeOH); IR(KBr) $v_{max}$: 2955, 1744, 1589, 1421, 1273, 1096 cm$^{-1}$; $^1$H NMR (CD$_3$OD, 400 MHz): δ9.25 (d, J=2.0 Hz, 1H), 9.19 (d, J=2.0 Hz, 1H), 8.77 (dd, J=5.1, 1.4 Hz, 1H), 8.74 (dd, J=5.0, 1.4 Hz, 1H), 8.53-8.50 (m, 1H), 8.47-8.45 (m, 1H), 8.05 (s, 1H), 7.60-7.54 (m, 1H), 7.14 (s, 1H), 6.99 (s, 1H), 3.73 (s, 3H), 3.52 (s, 3H), 2.50 (s, 3H), 3.15-2.46 (m, 7H); ESI-MS (30V): m/z (%) 538 [M+H]$^+$, 106 (100).

TEST EXAMPLE 1

Evaluation of Antioxidizing Activity in Free Radical Scavenging of 1,1-diphenyl-2-picryl-hydrazyl (DPPH)

An ethanolic solution of the stable nitrogen centered free radical 1,1-Diphenyl-2-picrylhydrazyl (DPPH, 100 μM) was incubated with the test compounds (10$^{-8}$-10$^{-4}$M) in 94-well plates, and then mixed thoroughly in a light-proof environment at room temperature. After 30 min, the absorbance (O.D.) was monitored spectrophotometrically at 517 nm. The activity in inhibiting free radical DPPH results in the decrease of absorbance.

The experimental results show that the test compounds 1-2 exhibit activity in free radical scavenging of DPPH at a concentration larger than about 10$^{-5}$ M, as shown in FIG. 1.

TEST EXAMPLE 2

Evaluation of Activity in Inhibiting Lipid Peroxidase

The assay was executed with reference to the method described in Biochem Biophys Res Commun. 1986; 135(3): 1015-1021. The assay conditions are shown as follows, and the results are shown in Table 1.

Assay Conditions:
(a) Source: Dunkin Hartley Guinea pig liver microsomes
(b) Substrate: Polyunsaturated fatty acid
(c) Vehicle: 1% DMSO
(d) Pre-Incubation Time/Temp: 15 minutes/37° C.
(e) Incubation Time/Temp: 20 minutes/37° C.
(f) Incubation Buffer: 0.25 M Potassium Phosphate, pH 7.4, 0.1 mM EDTA
(g) Quantitation Method: Spectrophotometric quantitation of Malondialdehyde

TABLE 1

| Compound No. | Species | Concentration | Inhibition (%) |
|---|---|---|---|
| 1 | guinea pig | 10 μM | 64 |
| 2 | guinea pig | 10 μM | 70 |

The experimental results in Table 1 show that the test compounds 1-2 exhibit activity in inhibiting lipid peroxidase.

TEST EXAMPLE 3

Evaluation of Antioxidizing Activity in Free Radical Scavenging of 2,2'-azobis(2-amidinopropane)dihydrochloride (AAPH)

In order to evaluate the effect of test compounds in scavenging hydrophilic peroxy radical, the experiment was executed with reference to the method described by Tsuchiya et al. (Methods Enzymol 1992; 213: 460-472). In the experiment, peroxides will react with fluorescent substances and thus inflect observed fluorescence intensity. Thereby, the effect of test compounds in free radical scavenging can be evaluated by measuring the variation of the fluorescence intensity after the addition of test compounds.

Figure 2:
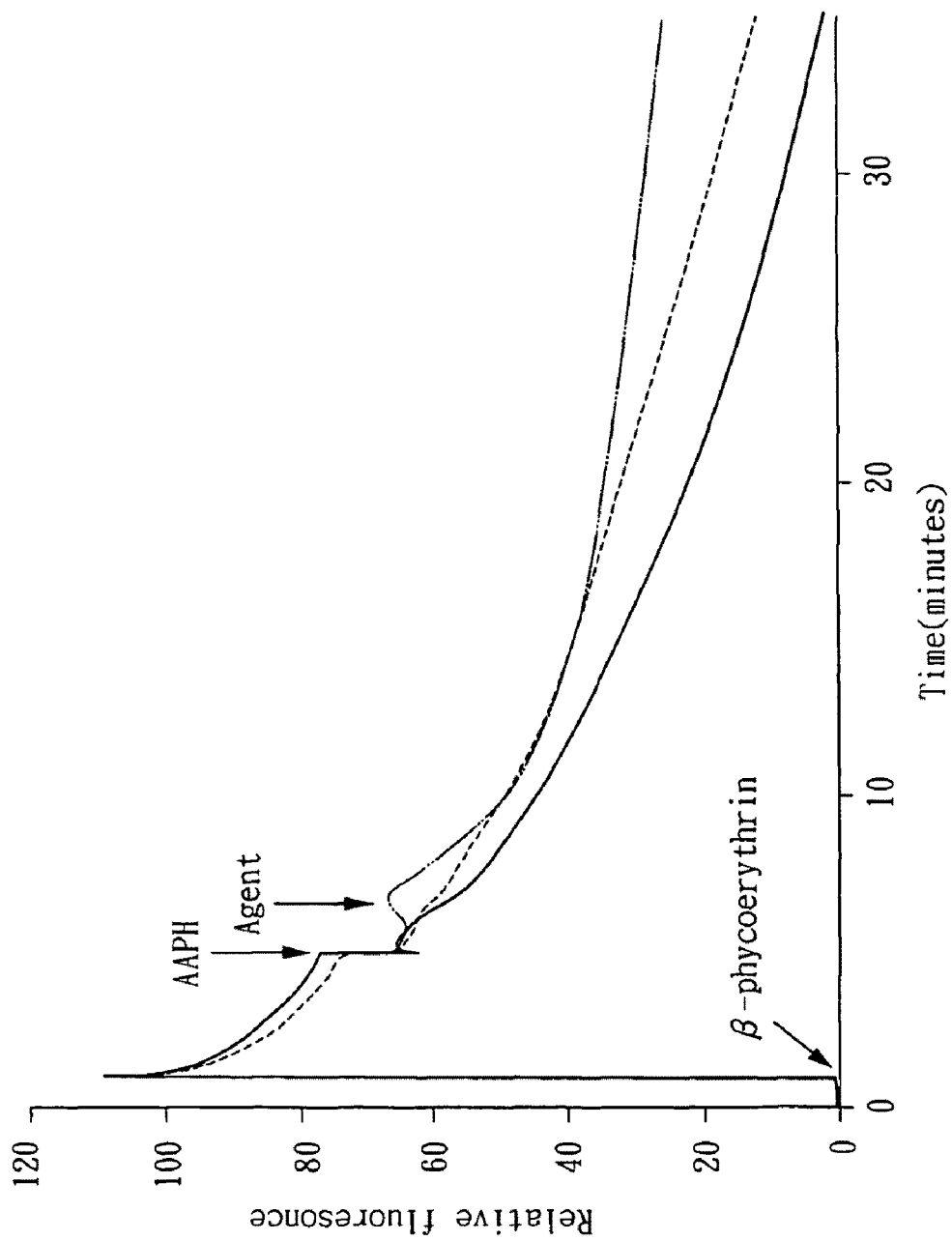
FIG. 2 shows a fluorescence decay dynamics of β-phycoerythin (——for 0.1% DMSO as a control group, - - - for Compound 1 of 5×10⁻⁶ M,——for Compound 2 of 5×10⁻⁶ M).

First, to a silicate tube was added a phosphate solution (2 ml, pH 7.4), followed by the addition of β-phycoerythrin (5 nM) to increase relative fluorescence intensity. After 5 minutes, 2,2'-azobis(2-amidinopropane)dihydrochloride (25 mM, AAPH) was added therein. Subsequently, through a fluorescent spectrometry (Shimadzu RF-5301PC, Japan), the fluorescence intensity of β-phycoerythrin was measured by excitation at 540 nm and emission at 570 nm. Then, the test compounds ($5 \times 10^{-6}$ M) was further added therein to observe the variation of the fluorescence intensity, in which 0.1% DMSO was taken as a control group. The results are shown in FIG. 2.

The experimental results show that the test compounds 1-2 can protect β-phycoerythin from peroxy radical AAPH—induced damage, and thus delay β-phycoerythin fluorescence degradation. Thereby, it can be confirmed that the test compounds 1-2 exhibit activity in free radical scavenging of APPH.

TEST EXAMPLE 4

Evaluation of Protecting Activity in Vascular Smooth Muscle Cells

Procedure

The vascular smooth muscle cells of rats ($2 \times 10^4$ cells/mL×1 mL) were quantitatively seeded in 24-well plates, and cultured in Dulbecco's modified Eagle medium (DMEM) with 10% fetal bovine serum (FBS) for 24 hours to achieve cell adhesion. After cell adhesion, the DMEM medium with 10% fetal bovine serum was replaced with a fresh DMEM medium with 0.1% fetal bovine serum to perform cell culture for 48 hours.

Figure 3:
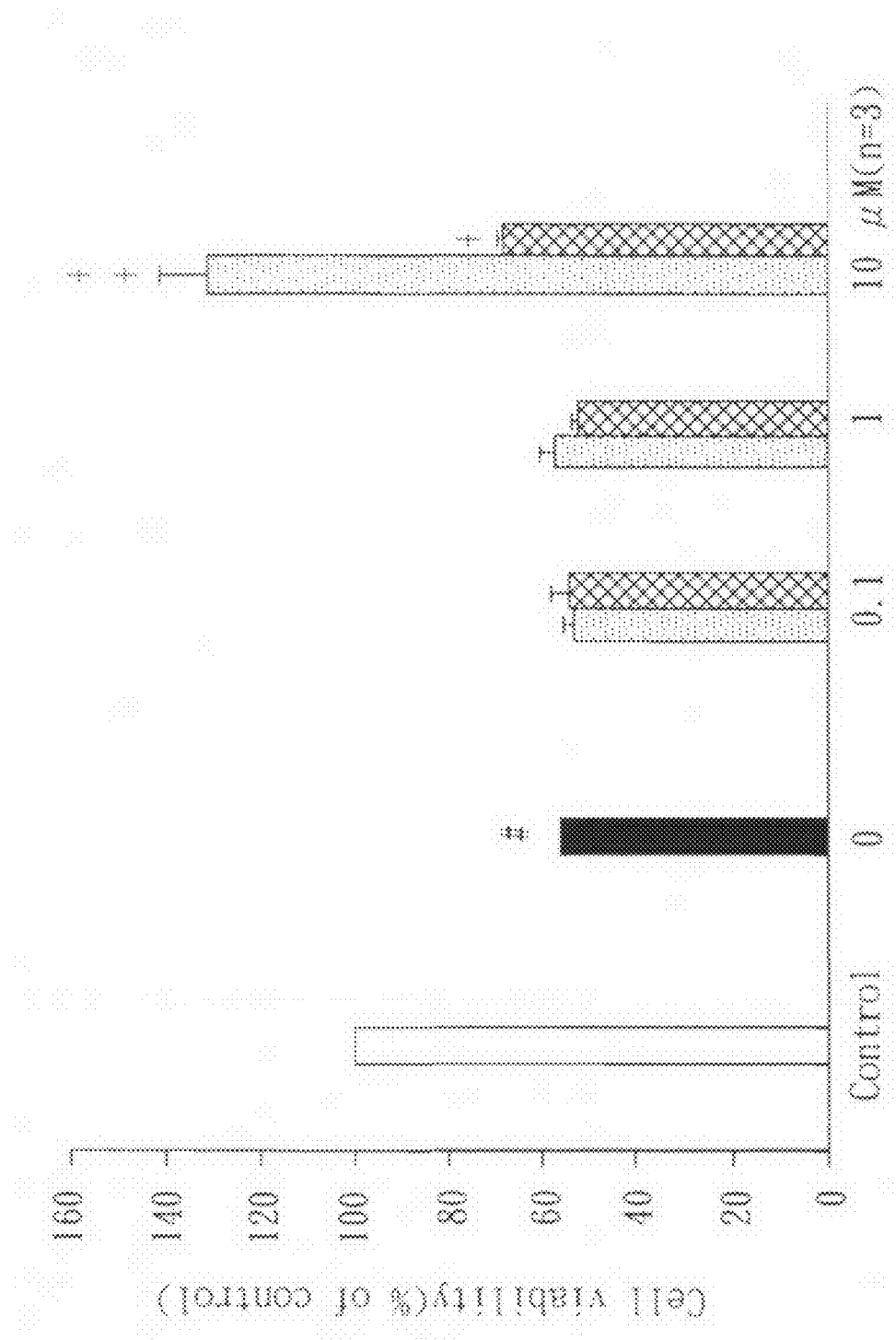
FIG. 3 shows a diagram of cell viability versus the concentration of Compounds 1 and 2 (□ for a control group, ■ for $H_2O_2$ of 200 μM, ▨ for Compound 1+$H_2O_2$ of 200 μM, ▨ for Compound 2+$H_2O_2$ of 200 μM).

Next, the test compounds were added in the cultures (final concentration: 0.1, 1, 10 μM). After 30 minutes, $H_2O_2$ (200 μM) was added therein to perform reaction for 24 hours in an incubator. Subsequently, in a light-proof environment, MTT (100 μL) was added into each well to perform reaction at 37° C. for 3 hours. The supernatant liquor was removed and then isopropanol (500 μL) was added, followed by shaking for 10 minutes. After standing for 10 minutes, supernatant liquor (200 μL) was transferred into 96-well plates. Finally, the absorbance values (O.D.) were monitored at 540 nm (OD540) and 630 nm (OD630). Based on the measured absorbance values (OD540-OD630), the effect of these test compounds on cell growth can be evaluated, as shown in FIG. 3.

Experimental Results

After $H_2O_2$ of various concentration and vascular smooth muscle cells of rats were maintained in the incubator to perform reaction for 24 hours at 37° C., concentration-dependent cytotoxicity by $H_2O_2$ was observed, in which $H_2O_2$ of a concentration larger than 100 μM resulted in cell death.

After these test compounds of various concentration (Compounds 1 and 2) reacted with vascular smooth muscle cells of rats for 30 minutes followed by adding $H_2O_2$ (200 μM) to perform reaction for 24 hours, it can be found that $H_2O_2$ (200 μM) significantly caused the decrease of cell number (# $P<0.05$), the test compound 2 (10 μM) can slightly inhibit $H_2O_2$ to damage vascular smooth muscle cells and the test compound 1 (10 μM) can significantly inhibit $H_2O_2$ to damage vascular smooth muscle cells and thereby increase cells survival rate (**$P<0.01$).

In view of the results of Test Examples 1-4, it can be confirmed that the compounds provided by the present invention are effective in inhibiting lipid peroxidase, exerting the free radical scavenging activities and protecting blood vessel smooth muscle cells and thus can reduce the oxidative stress that contribute to hypercholesterolemia, atherosclerosis, hypertension, diabetes, and heart failure etc., and ischemic cerebral diseases, including ischemic cerebral thrombosis, ischemic cerebral embolism, hypoxic ischemic encephalopathy etc.

Although the present invention has been explained in relation to its preferred embodiment, it is to be understood that many other possible modifications and variations can be made without departing from the scope of the invention as hereinafter claimed.

What is claimed is:

1. A compound of the formula (I):

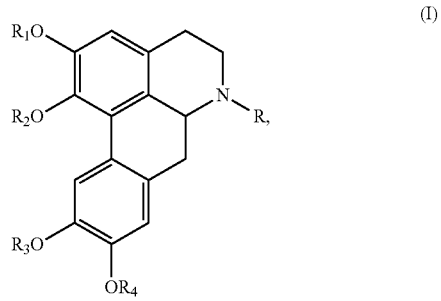

wherein
each of $R_1$, $R_2$, and R3, independently, is hydrogen, $C_{1-6}$ alkyl, or —C(O)$R_5$; $R_4$ is $C_{1-6}$ alkyl, or —C(O)$R_5$;
R is —C(O)$R_5$, or $C_{1-6}$ alkyl substituted by a member selected from the group consisting of:
(i) —C(O)O$R_6$,
(ii) —C(O)N$R_6R_7$,
(iii) at least two of —O$R_6$,
(iv) at least one of —N$R_6R_7$,
(v) $C_{4-9}$ heteroaryl containing at least one heteroatom selected from the group consisting of N, O and S, and
(vi) $C_{4-9}$ heterocyclyl containing at least one heteroatom selected from the group consisting of N, O and S;
$R_5$ is $C_{4-9}$ heteroaryl containing at least one heteroatom selected from the group consisting of N, O and S, or $C_{1-6}$ alkyl substituted by —N$R_6R_7$ or $C_{4-9}$ heterocyclyl containing at least one heteroatom selected from the group consisting of N, O and S;
each of $R_6$ and $R_7$, independently, is hydrogen, $C_{1-6}$ alkyl, $C_{4-9}$ heteroaryl containing at least one heteroatom selected from the group consisting of N, O and S, $C_{4-9}$ heterocyclyl containing at least one heteroatom selected from the group consisting of N, O and S, or $C_{6-10}$ aryl unsubstituted or substituted by at least one selected from the group consisting of halogen, hydroxyl, $C_{1-6}$ alkoxy and $C_{1-6}$ alkyl.

2. The compound of claim 1, wherein each of $R_1$, $R_2$, and R3, independently, is hydrogen or $C_{1-6}$ alkyl, $R_4$ is $C_{1-6}$ alkyl, and R is —C(O)$R_5$, or $C_{1-6}$ alkyl substituted by —C(O)O$R_6$, —C(O)N$R_6R_7$, two of —O$R_6$ or $C_{4-9}$ heteroaryl containing at least one heteroatom selected from the group consisting of N, O and S.

3. The compound of claim 2, wherein R is —C(O)$R_5$, or $C_{1-6}$ alkyl substituted by —C(O)N$R_6R_7$, $C_{4-9}$ heteroaryl containing at least one heteroatom selected from the group consisting of N, O and S, or both of hydroxyl and —O—$C_{6-10}$ aryl unsubstituted or substituted by at least one selected from the group consisting of halogen, hydroxyl, $C_{1-6}$ alkoxy and $C_{1-6}$ alkyl.

4. The compound of claim 3, wherein $R_6$ is hydrogen, and $R_7$ is $C_{4-9}$ heteroaryl containing at least one heteroatom selected from the group consisting of N, O and S, $C_{4-9}$ heterocyclyl containing at least one heteroatom selected from the group consisting of N, O and S, or $C_{6-10}$ aryl unsubstituted or substituted by at least one selected from the group consisting of halogen, hydroxyl, $C_{1-6}$ alkoxy and $C_{1-6}$ alkyl.

5. The compound of claim 4, wherein R is

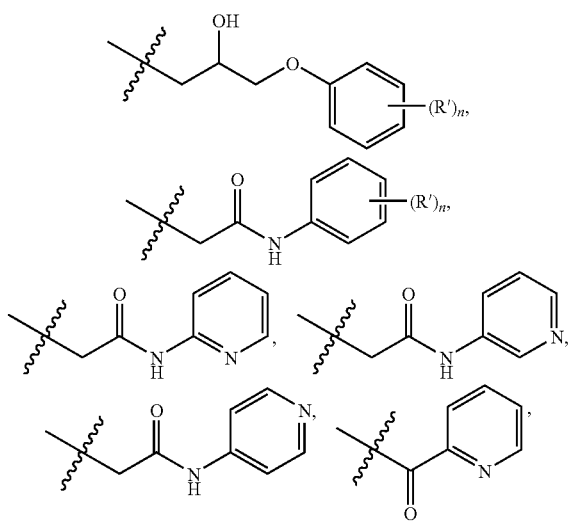

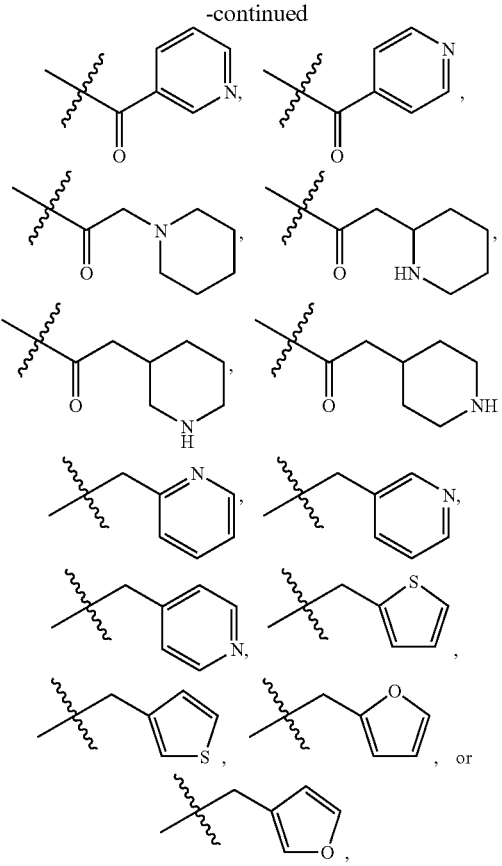

n being an integer from 0 to 5, and R' independently being halogen, hydroxyl, $C_{1-6}$ alkoxy or $C_{1-6}$ alkyl.

6. The compound of claim 1, wherein R is —C(O)$R_5$, or $C_{1-6}$ alkyl substituted by a member selected from the group consisting of:
(i) —C(O)O$R_6$,
(ii) —C(O)N$R_6R_7$,
(iii) at least two of —O$R_6$,
(iv) at least one of —N$R_6R_7$,
(v) $C_{4-9}$ heteroaryl containing at least one heteroatom selected from the group consisting of N, O and S, and
(vi) $C_{4-9}$ heterocyclyl containing at least one heteroatom selected from the group consisting of N, O and S.

7. A pharmaceutical composition comprising an effective amount of a compound according to claim 5 and a pharmaceutically acceptable carrier, wherein R is

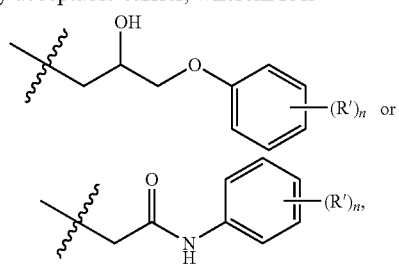

in which n is an integer from 0 to 5 and R' independently is halogen, hydroxyl, $C_{1-6}$ alkoxy or $C_{1-6}$ alkyl.

8. The pharmaceutical composition of claim 7, wherein R' independently is hydroxyl, $C_{1-6}$ alkoxy or $C_{1-6}$ alkyl.

9. The pharmaceutical composition of claim 7, wherein R' independently is methoxyl or methyl.

10. A pharmaceutical composition comprising an effective amount of a compound according to claim 6 and a pharmaceutically acceptable carrier.

11. A method for treating a disease chosen from at least one of atherosclerosis, hypertension and diabetes, comprising administering to a subject in need thereof a pharmaceutical composition according to claim 10.

12. A compound comprising a structure of the formula (I):

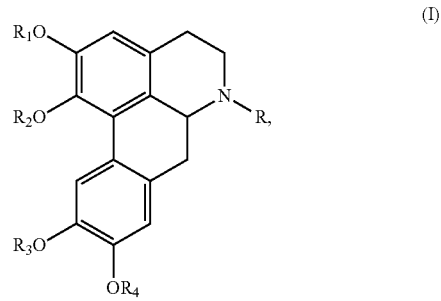

(I)

wherein
each of $R_1$, $R_2$, and $R_3$, independently, is hydrogen, $C_{1-6}$ alkyl, or —C(O)$R_5$; $R_4$ is $C_{1-6}$alkyl, or —C(O)$R_5$;
R is —C(O)$R_5$, or $C_{1-6}$alkyl substituted by a member selected from the group consisting of:
(i) —C(O)$NR_6R_7$,
(ii) at least two of —O$R_6$; and
(iii) $C_{4-9}$ heteroaryl containing at least one heteroatom selected from the group consisting of N, O and S,
$R_5$ is $C_{4-9}$ heteroaryl containing at least one heteroatom selected from the group consisting of N, O and S, or $C_{1-6}$ alkyl substituted by —$NR_6R_7$ or $C_{4-9}$ heterocyclyl containing at least one heteroatom selected from the group consisting of N, O and S;
each of $R_6$ and $R_7$, independently, is hydrogen, $C_{1-6}$ alkyl, $C_{4-9}$ heteroaryl containing at least one heteroatom selected from the group consisting of N, O and S, $C_{4-9}$ heterocyclyl containing at least one heteroatom selected from the group consisting of N, O and S, or $C_{6-10}$ aryl unsubstituted or substituted by at least one selected from the group consisting of halogen, hydroxyl, $C_{1-6}$ alkoxy and $C_{1-6}$ alkyl.

13. The compound of claim 12, wherein R is $C_{1-6}$alkyl substituted by at least two of —O$R_6$.

14. The compound of claim 13, wherein the compound is

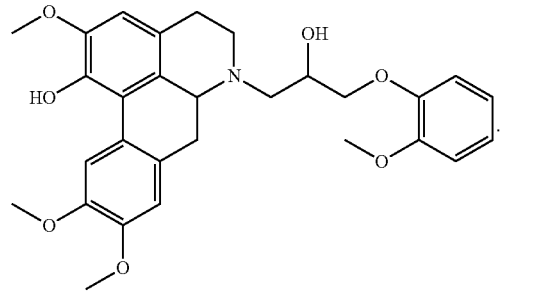

15. The compound of claim 12, wherein R is $C_{1-6}$ alkyl substituted by —C(O)$NR_6R_7$.

16. The compound of claim 15, wherein the compound is

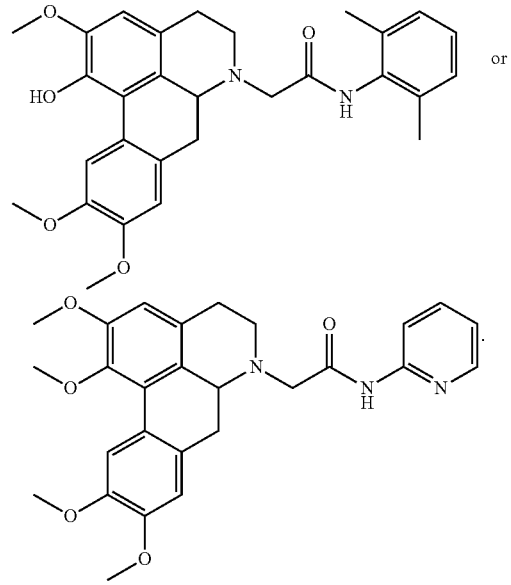

or

17. The compound of claim 12, wherein R is $C_{1-6}$ alkyl substituted by $C_{4-9}$ heteroaryl containing at least one heteroatom selected from the group consisting of N, O and S.

18. The compound of claim 17, wherein the compound is

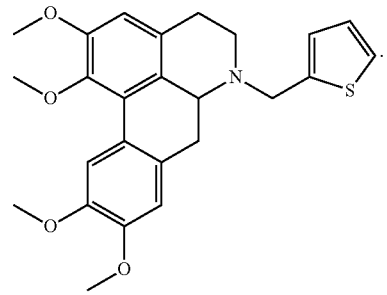

19. The compound of claim 12, wherein R is —C(O)$R_5$.

20. A compound of formula II:

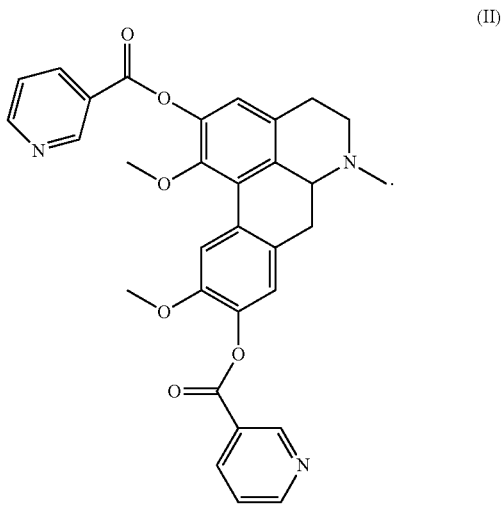

(II)

* * * * *